US005690943A

United States Patent [19]

Bourboulou et al.

[11] Patent Number: 5,690,943

[45] Date of Patent: Nov. 25, 1997

[54] STORAGE OF PARENTERALLY ADMINISTERABLE PRODUCTS

[75] Inventors: Yves Bourboulou, Rilhac-Rancon; Micheline Boucheteil, Saint-Yrieix-sous-Aixe; Céline Philippon, Limoges; Jean Tronchet, Couzeix, all of France

[73] Assignee: Pharmacia & Upjohn Aktiebolag, Stockholm, Sweden

[21] Appl. No.: 428,178

[22] PCT Filed: Nov. 2, 1993

[86] PCT No.: PCT/SE93/00915

§ 371 Date: Jun. 30, 1995

§ 102(e) Date: Jun. 30, 1995

[87] PCT Pub. No.: WO94/10064

PCT Pub. Date: May 11, 1994

[30] Foreign Application Priority Data

Nov. 3, 1992 [SE] Sweden .................................. 9203250

[51] Int. Cl.[6] ....................................................... A61K 9/00

[52] U.S. Cl. ............................. 424/400; 514/54; 514/558

[58] Field of Search ............................... 424/400; 514/54, 514/558, 873

[56] References Cited

U.S. PATENT DOCUMENTS

| | | | |
|---|---|---|---|
| 4,164,109 | 8/1979 | Dubois | 53/427 |
| 4,709,819 | 12/1987 | Lattuada et al. | 206/524.8 |
| 5,071,667 | 12/1991 | Grüne et al. | 426/396 |

FOREIGN PATENT DOCUMENTS

| | | |
|---|---|---|
| 0 093 796 A3 | 11/1983 | European Pat. Off. . |
| 0 220 152 A1 | 4/1987 | European Pat. Off. . |
| 0 510 687 A2 | 10/1992 | European Pat. Off. . |
| 2 344 008 | 10/1977 | France . |
| 2 406 567 | 9/1979 | France . |
| 211 309 | 4/1987 | New Zealand . |
| 216 390 | 9/1988 | New Zealand . |
| 8804186-8 | 3/1990 | Sweden . |
| 1 263 217 | 2/1972 | United Kingdom . |
| 2 178 702 | 9/1987 | United Kingdom . |

OTHER PUBLICATIONS

Bullock et al., Emulsion Stability in Total Nutrient Admixtures Containing a Pediatric Amino Acid Formulation, Jour. Parent. Enteral. Nutr., vol. 16, No. 1 (1992), pp. 64–68.

Rattenbury et al., Identification of the Cause of Separation (Creaming) of Lipid Emulsions in Intravenous Infusion, Jour. Ped. Gastroent. Nutr., vol. 8, No. 4 (1989), pp. 491–495.

Parry et al., Effect of various nutrient ratios on the emulsion stability of total nutrient admixtures, Am. Jour. Hosp. Pharm., vol. 43, No. 12 (1986), pp. 3017–3022.

Whateley et al., Particle Size Stability of Intralipid and Mixed Total Parenteral Nutrition Mixtures, Jour. Clin. Hosp. Pharm., vol. 9, No. 2 (1984), pp. 113–126.

Mayfield et al., Creaming and Plasma Clearance Rate of Intravenous Fat Emulsion in Critically Ill Patients, Clin. Nutr., vol. 3, No. 2 (1984), pp. 93–97.

*Primary Examiner*—James H. Reamer
*Attorney, Agent, or Firm*—Pollock, Vande Sande & Priddy

[57] ABSTRACT

The present invention is directed to the method and use of a helium containing gas for improving the physical stability of packaged sensitive products, especially those products which contain a fat emulsion.

21 Claims, No Drawings

STORAGE OF PARENTERALLY ADMINISTERABLE PRODUCTS

This application is a 371 of PCT/SE93/00915 filed Nov. 2, 1993.

FIELD OF INVENTION

The present invention is directed to the improvement of the physical stability of long-term stored products for parenteral use and especially those products comprising a fatty emulsion packaged in at least partially oxygen permeable containers.

BACKGROUND OF THE INVENTION

It is a considerable problem for manufacturers of products for parenteral administration that the products may deteriorate during the storage period from the packaging to their use in medical applications. This is an especially severe problem when storing chemically and physically complex liquid mixtures with several phases and constituents which to a certain extent are incompatible with each other. Examples of such sensitive products are fat emulsions for parenteral nutrition, which often will comprise further constituents, such as polysaccharides, amino acids, electrolytes and trace elements, with a negative influence both on the chemical and physical stability of the product.

In present technology it is frequently required to remove oxygen from the storage environment to improve the stability for oxygen sensitive products to which category fat emulsions also belong, due to their content of long chain polyunsaturated fatty acids. There are numerous disclosures of how nitrogen and certain rare gases have been employed in inventions having an oxygen depleted atmosphere for the storage of sensitive products. In the American patent U.S. Pat. No. 5,071,667, a method of packaging perishable foodstuffs in containers is disclosed, wherein a jet of preserving gas is directed to the unfilled portions of the containers to expel air before sealing. FR 2406567 discloses a packaging process related to the one described in the American patent, wherein a rare gas is used to conserve the contents of the packages.

It is state of the art when packaging fat emulsions, to fill them in packages made from a partially gas-permeable plastic material such as EVA and thereafter introducing them in an envelope, which is made of an airtight material and removing air with vacuum applying means before supplying nitrogen gas to restore the atmospherical pressure and finally sealing the envelope.

The use of nitrogen gas suffers from a disadvantage in that it is highly soluble in both in the aqueous phase and in the oil phase of a fat emulsion which leads to bubble forming when the packages are warmed up from a storage temperature of about 2°–8° C. to room temperature prior to the use. This is a problem during the administration, especially with infusion pumps, because many pumps alarm when bubbles are detected and the infusion is stopped.

Even if the use of the mentioned substantially oxygen-free atmospheres, optionally together with complementary oxygen scavengers, many times will lead to stored products which comply with the requirements of reducing or avoiding for example chemical oxygen dependent degradation of fats, it is still a considerable problem with a poor physical stability, especially products for total parenteral nutrition containing a fat emulsion.

Some of the most common physical stability problems in stored fat emulsions are creaming, flocculation and coalescence.

Creaming or cream formation is often formed during storage fat emulsion and appears as a cream-like layer on top of the emulsion. The phenomenon is to a certain extent reversible when shaking the container with stored emulsion. Flocculation appears when drops in an emulsion is added to each other and coalescence appears when the drops float together and exchange phospholipids, leading to a break-up of the emulsion. Flocculation and coalescence are irreversible phenomena.

Creaming is a technical problem for manufacturers of preparations for parenteral nutrition containing fatty emulsions and many attempts have been made overcome it, for example by adding stabilizing components, see EP 0 220 152 ( page 2, lines 26 to 34). The creaming phenomenon appears due to reversed sedimentation of the fat droplets which is a normal process in emulsions. The process is especially pronounced in solutions intended for total parenteral nutrition (TPN), where the addition of amino adds, electrolytes and trace elements, which often are positively charged ions, will reduce the surface charge of the lipid particles, causing them to aggregate and to form a cream layer, see also J Parent Enteral Nutr, 1992, 16 (1), p 64–8, Am J Hosp Pharm 1986, 43 (12), p 3017–22, J Parent Gastroenterol Nutr, 1989, 8 (4), p 491–5 and J Clin Hosp Pharm, 1984, 9 (2), p 113–26.

Clinically, creaming can cause serious complications in parenteral nutrition, because it may lead to an irregular lipid supply during the administration, which in certain cases may cause hazardous aggregations of lipid particles in the blood system. The clinical problems with creaming and fat emulsions which are unstable in-vivo are previously disclosed in, for example, EP 0 220 152 (page 2, lines 34 to 55) and Clin Nutr, 1984, 3 (2), p 93–7.

It is therefore highly desirable for manufacturers of fat emulsions to overcome or minimize any form of physical instability of fat emulsions and to find a way to store and administrate as many components of a parenteral solution together as possible.

To overcome the above-mentioned stability problems after storing, without adding surplus, potentially dangerous stabilizers, we have searched for alternative applications with other gaseous atmospheres. We have found that an atmosphere of helium or essentially composed of thereof is especially advantageous in solving the problems with gas bubble formation during administration and that such an atmosphere surprisingly increases the physical stability of the products for parenteral administration during storage in some important aspects.

Helium has previously been suggested as a substitute for nitrogen gas in the packaging of sensitive surgical articles as disposed in GB 1263217 or infusion fluids comprising fat emulsions EP 0 510 687 (page 7, lines 3 to 5). These documents suggests helium as an alternative inert gas for providing a substantially oxygen-free atmosphere for avoiding chemical degradation in terms of oxidation. However, it has not been previously disclosed that helium in any manner can lead to an improvement also in the physical stability of parenteral products comprising a fat emulsion.

DESCRIPTION OF THE INVENTION

The aim of the present invention is to improve the physical stability of a stored product. An especially favoured object of the invention is to improve storage of pre-packaged products for parenteral administration, which both are sensitive for air oxygen and possibly also physically unstable.

The invention is directed to a method for increasing the physical stability of a sensitive product for parenteral administration during long-term storage, comprising a fat emulsion wherein the said product is packaged in an at least one partially gas permeable primary container which is sealed in a substantially airtight envelope, in which method environmental air is removed from the envelope by applying vacuum generating means, whereafter the atmospherical pressure is restored by supplying a helium containing inert gas, preferably essentially composed of helium, and thereafter the envelope is finally sealed.

Another object of the invention is to use helium or a helium containing inert gas for increasing the physical stability of product for parenteral administration comprising a fat emulsion.

The invention is specially favourable for reducing creaming and for avoiding flocculation in such products.

The products disclosed herein comprises fat emulsions, glucose solutions, carbohydrates, amino adds, electrolytes, trace elements and any mixtures thereof, which may be packaged in a single compartment container as a mixture or in multi-compartment container for subsequent mixing before administration. The mentioned constituents are preferably solutions, but in various applications some may appear in solid form, for subsequent mixing. Any of the said constituents can further comprise one or several compounds with an additional therapeutical or diagnostical activity. Preferably, the products comprise components to be used as infusion solutions in therapy and/or nutrition.

The envelope or "secondary package" is made of an airtight flexible or semi-rigid material which can be an aluminum foil laminated with one or several polymer films. There are of course other airtight materials which may be used and anyone skilled in the art would be able to find out alternatives with the appropriate qualities. By the word "airtight" we mean a material that both can prevent the ambient atmosphere to penetrate the envelope and that prevents helium in the interior atmosphere to leak out in other ways than through slow diffusion.

The helium for the interior atmosphere can be taken from a variety of sources, but it will have to fulfil the USP monography. The term helium containing inert gas used in the present text is preferably a gas containing at least 50% helium, wherein other inert gases may be present. However, other compositions are also to be considered be a part of the present invention provided functionally inert alternatives can be added. Preferably, the helium atmosphere will consist of a dominating part of helium, but certain small amounts of other inert or rare gases are not considered to affect the improved storability of the products according to the present invention. Most preferred is a gas essentially composed of helium with minor amounts of other functionally inert gases.

The primary package containing the product for parenteral administration is preferably made of materials compatible with its contents, which are sensitive medical or nutritional compositions. One example of such a material is EVA (Ethylene Vinyl Acetate). EVA is often used as the major component in medical bags for storing infusion fluids with minor amounts of antioxidant additives and it is partially gas permeable. Other materials are of course also possible to use, but they are preferably compatible with materials to be used in medicine and in parenteral nutrition. The primary package can be single or multi-compartmented and can be provided with means to open the compartments for mixing of their contents immediately prior to the use.

The product to be protected during storage according to the invention can be any liquid or solid or semi-solid material that is easily perishable by the ambient atmosphere, but will always contain at least one unstable constituent. In applications where especially oxygen depleted conditions are required, an oxygen scavenger can be positioned in the space between the primary and secondary packages. Useful oxygen scavengers are for example described in the European Patent Specifications EP 0093 796 and EP 0268 848.

The process for the manufacture of the said sealed envelope is principally performed by the following steps. The primary packages, which can be plastic bags, are aseptically filled with their contents in a sterilized isolator and thereafter weight controlled and sealed by welding, The assembly of the envelope is thereafter performed by placing the primary package or packages in the envelope, removing air by a connection to vacuum, produced by conventional vacuum generating means. The atmospherical pressure is restored by supplying a helium containing gas or a gas essentially composed of helium and thereafter is the envelope welded and sealed, The finished product is preferably stored at a temperature between 2°–8° C.

For the use in parenteral administration the envelope is opened just prior to the administration and the helium atmosphere is allowed to evaporate. The primary package containing fluids for parenteral administration will then be handled as any ordinary package or bag containing infusion solutions to be administered to a patient. The fluids will initially contain a certain amount of dissolved helium which gradually will evaporate during the administration due to its volatility.

The use of a helium containing inert gas or an atmosphere essentially composed of helium for the storage of a package of parenterally administerable fluids solves the problem with gas bubble formation during administration at room temperature. This appears to be caused of the low solubility of helium both in fats and in aqueous solutions, The solubility of helium in fats is about one sixth of that of nitrogen, and the solubility of helium in aqueous solutions decrease seven times less than the solubility of nitrogen, when the temperature rises from 0° C. to 30° C. The solubility values in Table 1 below show that helium is less soluble than nitrogen in all the tested fluids, and most notably in lipids, a major constituent of many important nutrients for parenteral use.

TABLE 1

SOLUBILITY OF INERT GASES ($N_2$ AND HE) IN WATER, PLASMA, AND LIPIDS AT 37° C.
In ml of gas/ml of fluid at 1013 hPa

| | WATER | PLASMA | LIPIDS | BLOOD |
|---|---|---|---|---|
| NITROGEN | 0.0144 | 0.013 | 0.07 | 0.016 |
| HELIUM | 0.0100 | 0.0086 | 0.017 | 0.010 |

The gas bubbles observed when the nutrient is warmed up to room temperature are caused by the decline in the solubility of the nitrogen (−0.8%/°C.) as the temperature rises. The solubility of helium increases, as a contrast, when the temperature rises (+0.3%/°C.). The solubility coefficients and their variation in response to temperature changes reveal that fluids stored under influence of helium contain no gas bubbles when reheating. The probability of injecting bubbles will be dose to zero when administering a helium stored fluid. If, due to some handling error, a helium bubble is accidentally administered, it would dissolve much more rapidly in plasma than a similar nitrogen bubble because of the lack of dissolved helium in the body fluids. Besides that, the amounts of dissolved helium from a helium saturated nutrient will not be able to induce any toxic effects in humans at atmospherical pressure. The amount of dissolved helium in a nutrient can be evaluated and compared with the quantity of helium dissolved in the blood of a diver diving to the saturation depth of 300 m.

Helium dissolved in a bag of nutrient (2200 $cm^3$), assuming total saturation will be:

Lipids 600 $cm^3$, or 10.2 $cm^3$ of helium

Aqueous sol. 1600 $cm^3$, or 16.0 $cm^3$ of helium which makes the total amount of helium to 26.2 $cm^3$ (not corrected for temperature adjustments). This should be compared with the amount of helium dissolved in 5 l of blood of a diver breathing a mixture defined of $pO_2$=0.45 bar; $pN_2$=0.8 bar and pHe=29.75 bar (the classical mixture used in saturation diving to 300 m (31 ATA)). It would give an amount of 1488 $cm^3$ helium in the blood of a diver (pHe×5000×solubility=1488 $cm^3$) breathing the helium/oxygen mixture at a depth of 300 m, which is 60 times more than the theoretical maximum content of helium dissolved in a bag of intravenous nutrients stored in an helium atmosphere.

The stability of products stored in an atmosphere essentially composed of helium is evaluated in tests showing that KabiMix Novum 740 (A TPN-mixture containing a lipid emulsion and a solution of amino adds, glucose and electrolytes) is physically and chemical stable for six months when stored in an atmosphere essentially composed of helium at a temperature of 5±3° C. The studied parameters are residual oxygen, pH, osmolality, mean droplet size and visual inspections of creaming and emulsion appearance for batches stored under a nitrogen atmosphere compared to those stored under a helium atmosphere. The tests confirm that residual oxygen, pH, oxygen and mean drop size distribution is unchanged during helium storage. The visual tests indicate that helium storage improve the visual appearance (see Table 2 below).

Tables 2A and 2B shows comparisons of visual emulsion appearance for different batches stored under nitrogen and helium. The visual inspection tries to define the free oil formation on surface of the cream layer. The tested products are judged to acceptable or refused according to predetermined standards.

Stability tests are also successfully performed for a preparation for total parenteral nutrition containing a lipid emulsion and a solution of amino adds and glucose, which subsequently have led to a registered product, KabiMix 2400 kcal, packed under helium with a six months shelf-life. These tests also confirm that helium stored preparations are physically stable for at least six months at a temperature of 5±3° C. The studied parameters were residual oxygen, pH, osmolality, particle size distribution and visual inspections of the appearance of the product and the creaming layer.

Tables 3A to C shows a creaming determination performed visually by inspecting bags filled with KabiMix 2400 kcal stored under nitrogen or helium. The results of Tables 3A to C show that creaming in millimeters are reduced when using helium as a storage medium.

The creaming effect is to a certain extent a reversible phenomenon, so when a package or a bag containing the mixture is squeezed or agitated will the effect decrease. The reversibility of creaming will be especially distinct if helium is used as a protective gas and the nutrient solution will thus be easier to redisperse before administration.

The present studies also show that trace elements can be incorporated in mixture for total parenteral nutrition with a shelf life up to two months and possibly longer, without coloration of the mixture provided helium and oxygen scavengers are used. This is yet another advantageous improvement in storage of parenteral solutions provided by the present invention.

Table 4 shows the stability results for a TPN-preparation comparable to the KabiMix products with incorporated trace elements.

The results from Tables 2 to 4 clearly show that helium provides excellent protection from chemical degradation from oxygen and also a surprising benefit in the physical stability, such as creaming, when compared to nitrogen storage. It is clearly apparent that helium possibly in a dissolved for has an influence on the emulsion stability.

Helium storage according to the present invention will provide an opportunity to prolong safe storage of products for parenteral nutrition and especially those having added compounds for total parenteral nutrition.

What has been stated above reveals the matters and advantages of the present invention that others readily can apply and adapt within the current knowledge. Any such applications and adaptations of the present invention are intended to be comprehended within the meaning and range of the appended claims.

TABLE 2A

VISUAL INSPECTION
EMULSION APPEARANCE DETERMINATION
CONCLUSION ACCORDING TO STANDARD CODIFICATION

| Test schedule (months) | BATCHES UNDER NITROGEN Mean value of 3 bags BATCHES No. 1 | No. 2 | No. 3 |
|---|---|---|---|
| 0 | A | A | A |
| 1 | A | A | A |
| 2 | A | A | A |
| 3 | A | A | A |
| 4 | A | A | A |
| 5 | R | R | R |
| 6 | R | R | R |

| Test schedule (months) | BATCHES UNDER HELIUM Mean value of 3 bags BATCHES No. 4 | No. 5 |
|---|---|---|
| 0 | A | A |
| 1 | A | A |
| 2 | A | A |
| 3 | A | A |
| 4 | A | A |
| 5 | A | A |
| 6 | A | A |

A: Acceptable
R: Refused

TABLE 2B

BATCH No. 4 COMPARED STORAGE UNDER NITROGEN AND HELIUM

| Test schedule (months) | Mean value of 2 determinations made on 2 bags Nitrogen | Helium |
|---|---|---|
| 3 | R | A |
| 4 | R | A |
| 5 | R | A |
| 6 | R | A |

A: Acceptable
R: Refused

TABLE 3A

KABI MIX 2400 KCAL UNDER NITROGEN
VISUAL INSPECTION
Creaming in bags in mm
Mean value of 2 determinations made on 2 bags
VISUAL INSPECTION IN BAGS

| Storage time | Creaming in mm BATCHES | | |
|---|---|---|---|
| (days) | No. 6 | No. 7 | No. 8 |
| 0 Beginning | 0 | 1,3 | 0 |
| End | 0 | 1,5 | 0 |
| 15 | 1,5 | 3 | 1,5 |
| 30 | 4 | 4 | 2,5 |
| 45 | 4 | 7,8 | 4 |
| 60 | 7 | 8 | 5,5 |
| 75 | 3,5 | 8,5 | 5,5 |
| 90 | 6 | 11,5 | 8,5 |
| 120 | 6 | 7 | 6,5 |

TABLE 3B

KABI MIX 2440 KCAL UNDER HELIUM
VISUAL INSPECTION IN BAGS

| Storage time | Creaming in mm Mean value of 2 determinations made on 2 bags | | |
|---|---|---|---|
| (days) | Batch No. 9 | Batch No. 10 | Batch No. 11 |
| 90 | 1 | 1 | 0,5 |
| 120 | * | * | 0,7 |
| 180 | 1 | 1 | 0,8 |

*not studied

TABLE 3C

KABI MIX 2440 KCAL FROM THE SAME BATCH UNDER NITROGEN AND HELIUM
VISUAL INSPECTION IN BAGS

| Storage time | Creaming in mm Average value of 4 bags | |
|---|---|---|
| (months) | nitrogen | helium |
| 3 | 7 | 1 |
| 4 | 5 | 1 |
| 5 | 7 | 2 |
| 6 | 4 | 2 |

TABLE 4

PHYSICAL STABILITY RESULTS FOR TPN FORMULA INCORPORATING TRACE ELEMENTS

| VISUAL INSPECTION in bag | Study period in moths | Formula packed under He without $O_2$ scavengers | Formula packed under He with $O_2$ scavengers |
|---|---|---|---|
| Creaming in mm | 1 | 12 | 10 |
| | 2 | 13 | 12 |
| Cream layer colouring | 1 | yellow | OK |
| | 2 | yellow | OK |
| Emulsion appearance determination in bag | 1 | A | A |
| | 2 | A | A |

We claim:

1. Method of increasing the physical stability of a product for parenteral administration comprising a lipid emulsion packaged in an at least partially gas permeable container which comprise storing said lipid emulsion in an inert gas consisting essentially of helium.

2. Method according to claim 1 wherein creaming of said emulsion is reduced or flocculation of said emulsion is avoided or both.

3. Method according to claim 1 wherein said product further comprises at least one constituent selected from the group consisting of glucose, polysaccharides, amino acids, electrolytes, trace elements, therapeutically active compounds and mixtures thereof.

4. Method according to claim 3 wherein said product is suitable for total parenteral nutrition.

5. Method according to claim 1 wherein said gas permeable container is made of a polymer material not completely impermeable to oxygen.

6. Method according to claim 1, wherein the gas permeable container is enclosed in an airtight envelope with an inert gas atmosphere consisting essentially of helium.

7. Method according to claim 5 wherein said polymer material is a polymer of ethylene and vinyl acetate.

8. Method according to claim 6 wherein said airtight envelope is an aluminum foil laminated with one or more polymer films.

9. A method of manufacturing a package for improving the physical stability of a parenteral product comprising a lipid emulsion which comprises packaging said parenteral product in a partially gas permeable container to provide a packaged product;

thereafter placing the packaged product in a substantially airtight envelope;

then removing environmental air from said envelope by drawing a vacuum;

then restoring atmospheric pressure by supplying an inert gas consisting essentially of helium and then sealing said envelope.

10. Method according to claim 9 wherein creaming of said emulsion is reduced or flocculation of said emulsion is avoided or both.

11. Method according to claim 9 wherein said product further comprises at least one constituent selected from the group consisting of glucose, polysaccharides, amino acids, electrolytes, trace elements, therapeutically active compounds and mixtures thereof.

12. Method according to claim 9 wherein said product is suitable for total parenteral nutrition.

13. Method according to claim 9 wherein said gas permeable container is made of a polymer material not completely impermeable to oxygen.

14. Method according to claim 13 wherein said polymer material is a polymer of ethylene and vinyl acetate.

15. Method according to claim 9 wherein said airtight envelope is an aluminum foil laminated with one or more polymer films.

16. A packaged parenteral product exhibiting improved physical stability during long-term storage which comprises a parenteral product comprising a lipid emulsion packaged in a partially gas permeable container and sealed in a substantially airtight envelope containing an inert gas consisting essentially of helium and being free of environmental air.

17. The packaged parenteral product of claim 16 wherein said parenteral product further comprises at least one constituent selected from the group consisting of glucose, polysaccharides, amino acids, electrolytes trace elements, therapeutically active compounds and mixtures thereof.

18. The packaged parenteral product of claim 16 wherein said product is suitable for total parenteral nutrition.

19. The packaged parenteral product of claim 16 wherein said gas permeable container is made of a polymer material not completely impermeable to oxygen.

20. The packaged parenteral product of claim 19 wherein said polymer material is a polymer of ethylene and vinyl acetate.

21. The packaged parenteral product of claim 16 wherein said airtight envelope is an aluminum foil laminated with one or more polymer films.

* * * * *